United States Patent
Yoshimura et al.

(10) Patent No.: US 9,402,598 B2
(45) Date of Patent: Aug. 2, 2016

(54) ULTRASOUND PROBE AND ULTRASOUND DIAGNOSTIC DEVICE USING SAME

(75) Inventors: Yasuhiro Yoshimura, Kasumigaura (JP); Tatsuya Nagata, Ishioka (JP); Akifumi Sako, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 79 days.

(21) Appl. No.: 13/817,541

(22) PCT Filed: Aug. 19, 2011

(86) PCT No.: PCT/JP2011/068811
§ 371 (c)(1),
(2), (4) Date: Feb. 19, 2013

(87) PCT Pub. No.: WO2012/023619
PCT Pub. Date: Feb. 23, 2012

(65) Prior Publication Data
US 2013/0172750 A1 Jul. 4, 2013

(30) Foreign Application Priority Data
Aug. 20, 2010 (JP) .................... 2010-184882

(51) Int. Cl.
| | |
|---|---|
| *A61B 8/00* | (2006.01) |
| *A61B 8/14* | (2006.01) |
| *B06B 1/02* | (2006.01) |
| *G10K 11/00* | (2006.01) |

(Continued)

(52) U.S. Cl.
CPC .................. *A61B 8/4444* (2013.01); *A61B 8/14* (2013.01); *A61B 8/4494* (2013.01); *B06B 1/0292* (2013.01); *G01N 29/2456* (2013.01); *G10K 11/002* (2013.01); *A61B 8/0883* (2013.01); *A61B 8/0891* (2013.01)

(58) Field of Classification Search
CPC ...... A61B 8/4444; A61B 8/14; A61B 8/4494; A61B 8/0891; A61B 8/0883; B06B 1/0292; G10K 11/002; G01N 29/2456
USPC ......................................... 600/459
See application file for complete search history.

(56) References Cited

U.S. PATENT DOCUMENTS

| | | | |
|---|---|---|---|
| 6,714,484 B2 | 3/2004 | Ladabaum et al. | |
| 7,358,650 B2 * | 4/2008 | Kondo et al. | 310/334 |

(Continued)

FOREIGN PATENT DOCUMENTS

| | | |
|---|---|---|
| JP | 60-102096 A | 6/1985 |
| JP | 2007-201753 A | 8/2007 |

(Continued)

OTHER PUBLICATIONS

Shung. Diagnostic Ultrasound Imaging and Blood Flow Measurements. 2006.*

*Primary Examiner* — Long V Le
*Assistant Examiner* — Colin T Sakamoto
(74) *Attorney, Agent, or Firm* — Mattingly & Malur, PC

(57) ABSTRACT

In order to obtain a high-resolution ultrasound diagnostic image while reducing the back side reflection of a ultrasound irradiated to the side opposite to the ultrasound transmission direction of an ultrasound transmission/reception device, disclosed is an ultrasound probe, wherein a substrate is provided thereon with a cavity, insulation layers having the cavity therebetween, and an upper layer electrode and a lower layer electrode having the cavity and the insulation layers therebetween, so as to form an ultrasound vibration element, the substrate is held by a backing with a low-modulus member therebetween, and a direct voltage and a alternating voltage are applied between the electrodes to vibrate the ultrasound vibration element, and wherein a mechanical impedance by the substrate and the low-modulus member has a substantially equal value as an acoustic impedance of the backing.

11 Claims, 7 Drawing Sheets

(51) Int. Cl.
*G01N 29/24* (2006.01)
*A61B 8/08* (2006.01)

(56) References Cited

U.S. PATENT DOCUMENTS 8,408,063 B2 * 4/2013 Sano et al. .................. 73/632
2008/0098816 A1 5/2008 Yamashita et al.
2009/0069688 A1 3/2009 Aono et al.
2010/0242612 A1 9/2010 Sano et al.

FOREIGN PATENT DOCUMENTS

| JP | 2008-118212 A | 5/2008 |
| JP | 2008-119318 A | 5/2008 |
| WO | 2009/069555 A1 | 6/2009 |
| WO | WO 2009069555 A1 * | 6/2009 |

* cited by examiner

ULTRASOUND PROBE AND ULTRASOUND DIAGNOSTIC DEVICE USING SAME

TECHNICAL FIELD

This invention relates to an ultrasound probe for acquiring diagnostic images and an ultrasound diagnostic device using that ultrasound probe.

BACKGROUND ART

An example of the conventional ultrasound probe in the field of inspecting a test object with ultrasound is disclosed in Patent Literature 1 cited below. This invention is structured with a gap, insulation layers, and electrodes formed on a silicon substrate. A damping material having substantially the same acoustic impedance as that of the silicon substrate is introduced into the opposite surface of the substrate. A DC voltage is applied between the electrodes and the silicon substrate so as to reduce the gap to a predetermined position. In this structure, an AC voltage is further applied in a manner contracting or expanding the gap in order to transmit ultrasound. The ultrasound probe also has the function of receiving the reflected ultrasound from the test object so as to detect a capacitance change between the electrodes and the silicon substrate. Here, the damping material plays the role of reducing ultrasonic wave reflection during transmission and reception. A specific damping material is prepared by mixing epoxy resin and tungsten particles in varying blending ratios, whereby the acoustic impedance of the material is adjusted to that of the silicon substrate.

Also, Patent Literature 2 cited below discloses an ultrasound probe having a piezoelectric element disposed on an acoustic backing with an acoustic impedance of 1.3 to 6 MRayls. The acoustic backing is described as a composite material mixed with zinc oxide fiber.

Furthermore, Patent Literature 3 cited below describes a CMUT (Capacitive Micromachined Ultrasonic Transducer) chip bonded with a backing to provide short pulses, i.e., a wideband ultrasonic waveform suitable for high-resolution use.

CITATION LIST

Patent Literature

Patent literature 1: U.S. Pat. No. 6,714,484B2
Patent literature 2: Japanese Patent Application Laid-Open Publication No. 2008-118212
Patent literature 3: Japanese Patent Application Laid-Open Publication No. 2008-119318

SUMMARY OF INVENTION

Technical Problem

The ultrasound probe for use with an ultrasound diagnostic device transmits ultrasound waves to a test object, receives the ultrasonic waves reflected from the test object, and turns the received ultrasonic waves into an image. Ultrasonic waves have the nature of reflecting from an interface between materials having different acoustic impedances. For this reason, a drop in image quality can result from ultrasonic waves reflecting from interfaces between an ultrasound transmission/reception device constituting the ultrasound probe, an acoustic lens disposed on the front side of the device, and the backing on the back side. The primary method of reducing reflection on the front side involves providing between the acoustic lens and the ultrasound transmission/reception device a matching layer having an intermediate acoustic impedance. Then there exists the frequently adopted technique of attenuating ultrasonic waves reaching the back side in the backing by making the acoustic impedance of the backing equal to that of the ultrasound transmission/reception device. However, the reflection from the back side stems from factors intrinsic to the CMUT, as will be described below. This has made it difficult for the conventional methods of equalizing acoustic impedances to reduce the ultrasonic wave reflection.

An object of this invention is to seek the cause of the above-mentioned back side reflection and take appropriate countermeasures to reduce the reflection of ultrasonic waves emitted from the ultrasound transmission/reception device to the back side, thereby obtaining high-quality diagnostic images.

More specifically, it has been found that in the CMUT-equipped probe, vibrations applied to a membrane over a cavity are propagated to the silicon substrate via a narrow rim supporting the membrane and that while being dispersed cylindrically within the silicon substrate, the vibrations engender reflection. This invention thus aims to provide a structure for preventing the acoustic reflection on the back side over the wideband.

Solution to Problem

In achieving the foregoing object of this invention and according to one aspect thereof, there is provided an ultrasound probe including an ultrasound vibration element constituted on a substrate by a cavity, by insulation layers with the cavity interposed therebetween, and by an upper layer electrode and a lower layer electrode with the cavity and the insulation layers interposed therebetween, the substrate being supported by a backing with a low-modulus member interposed therebetween, the ultrasound vibration element being vibrated by application of a direct-current voltage and an alternate-current voltage between the electrodes. The backing has an acoustic impedance falling within $\pm 1$ MRayls ($10^6$ kg/m$^2$ s) of a mechanical impedance formed by the substrate and the low-modulus member.

According to another aspect of this invention, there is provided an ultrasound diagnostic device for obtaining an ultrasound diagnostic image of a test object using the ultrasound probe outlined above.

Advantageous Effects of Invention

This invention provides an ultrasound probe capable of reducing the reflection of ultrasonic waves emitted from an ultrasound transmission/reception device to the back side thereof. The invention further provides an ultrasonic diagnostic device capable of presenting high-quality diagnostic images using the ultrasound probe of this invention.

BRIEF DESCRIPTION OF DRAWINGS

FIG. 2 is a cross-sectional view of an ultrasound transmission/reception device, a backing, an acoustic lens and the like.

DESCRIPTION OF EMBODIMENTS

A preferred embodiment of this invention is explained below in reference to FIGS. 1 through 14.

Figure 1:
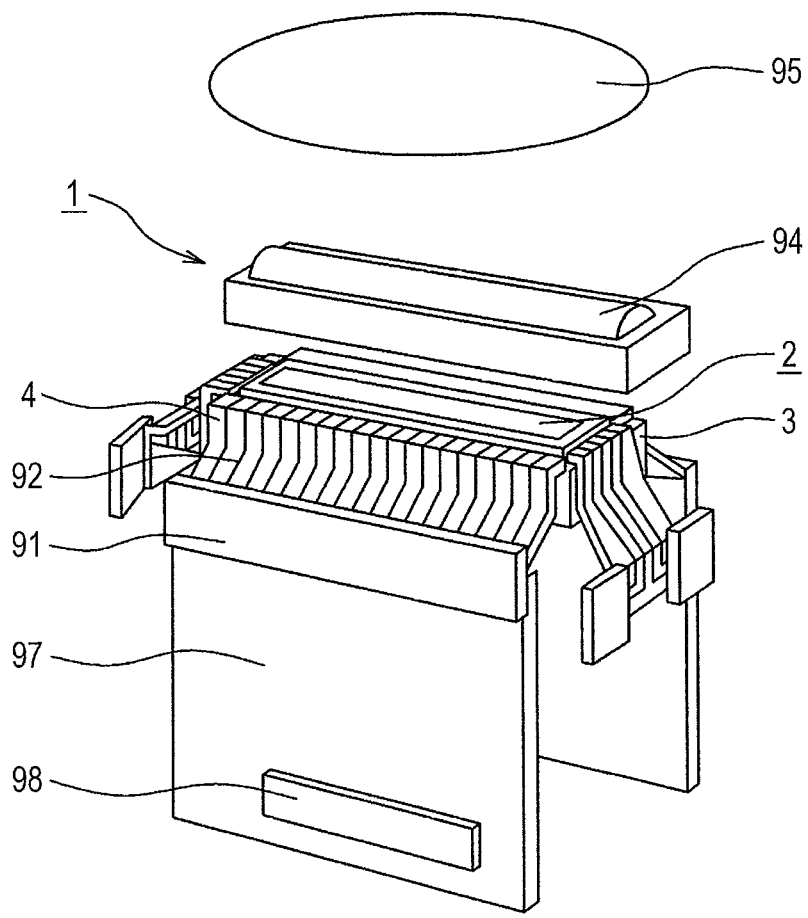
FIG. 1 is a schematic view showing an overall structure of an ultrasound probe.

FIG. 1 shows an overall structure of an ultrasound probe 1 furnished with an ultrasound transmission/reception device (ultrasound vibration element) 2. The ultrasound probe 1 is used at medical institutions in examining the human organism (examination of the heart, blood vessels, and other circulatory organs; abdominal examination and the like). The ultrasound probe 1 has a backing 3 tipped with the ultrasound transmission/reception device 2. A flexible substrate 4 having wiring 92 leading to a connector 91 is bonded to the ultrasound transmission/reception device 2 by wire bonding. The connector 91 is connected to a circuit substrate 97, and a connecting terminal 98 of the circuit substrate 97 is connected to an ultrasound diagnostic device. The ultrasound diagnostic device drives the ultrasound transmission/reception device 2 by giving it an electrical signal and turns a signal representing the reflected ultrasonic waves from the test object into an image. The surface of the ultrasound transmission/reception device 2 is furnished with an acoustic lens 94 of silicon resin designed to focus the ultrasonic waves generated by the ultrasound transmission/reception device 2 in the direction of the test object. The ultrasound transmission/reception device 2 transmits and receives ultrasonic waves to and from a test object 95 such as the human organism through the acoustic lens 94.

Figure 2:
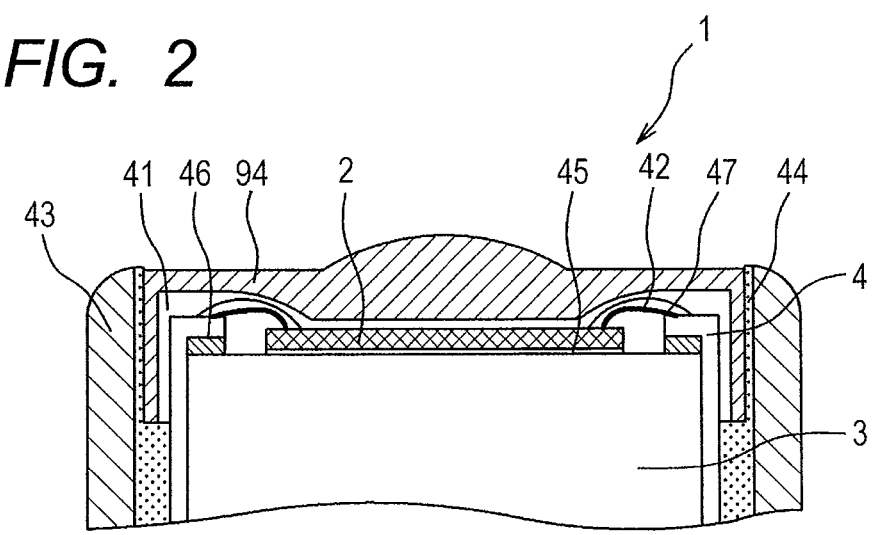

FIG. 2 is a cross-sectional view showing the acoustic lens 94, the ultrasound transmission/reception device (ultrasound vibration element) 2, and the backing 3 of the ultrasound probe 1 indicated in FIG. 1 along with surrounding constructs. The ultrasound transmission/reception device 2 is disposed on the backing 3 with a resin 45 interposed therebetween. The flexible substrate 4 for communicating ultrasound transmission/reception signals with the substrate (not shown) is also fixed to the backing 3 with a resin 46 interposed therebetween. The ultrasound transmission/reception device 2 and the flexible substrate 4 are bonded by wire bonding using a wire 42. The wire 42 and the surroundings of where it is bonded are sealed by a sealing resin 47. The sealing has the effect of securing the wire 42 and preventing electro-migration caused by application of a drive voltage. Onto these constructs, the acoustic lens 94 is fixedly bonded using a resin 41. Also, these constructs are structured to be housed in a case 43. The gap between the case 43 and an acoustic lens 2 is filled with a resin 44.

Figure 3:
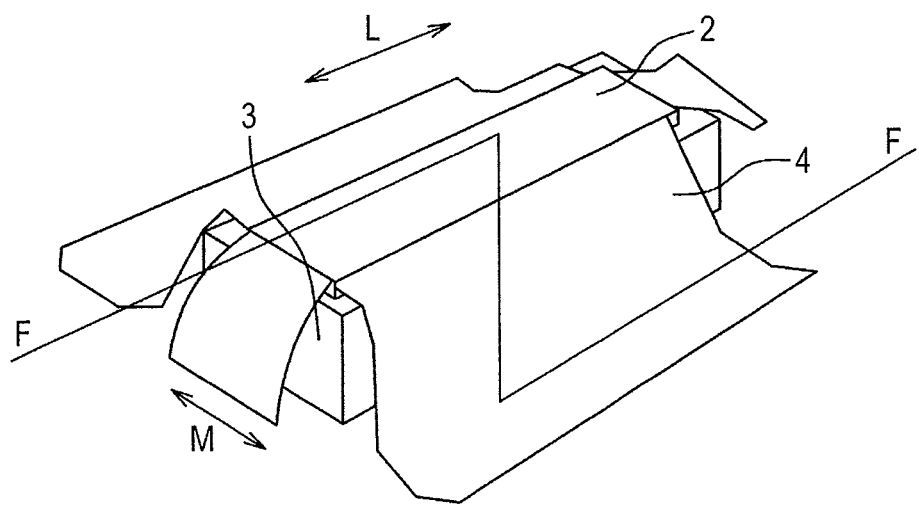
FIG. 3 is a perspective view showing the ultrasound transmission/reception device, the backing, and a flexible substrate.

FIG. 3 shows the ultrasound transmission/reception device 2, the backing 3, and the flexible substrate 4 explained in reference to FIG. 1. The long side direction of the ultrasound transmission/reception device 2 and backing 3 is indicated as a long axis direction L and the short side direction thereof as a minor axis direction M. The ultrasound transmission/reception device 2 is bonded onto the backing 3 by resin. The ultrasound transmission/reception device 2 is connected with the flexible substrate 4 for power supply and signal transmission. The flexible substrate 4 and backing 3 are bonded together, and electrode pads (not shown) of the ultrasound transmission/reception device 2 and wiring pads (not shown) of the flexible substrate 4 are interconnected (not shown) by wire bonding as indicated in FIG. 2.

Figure 4:
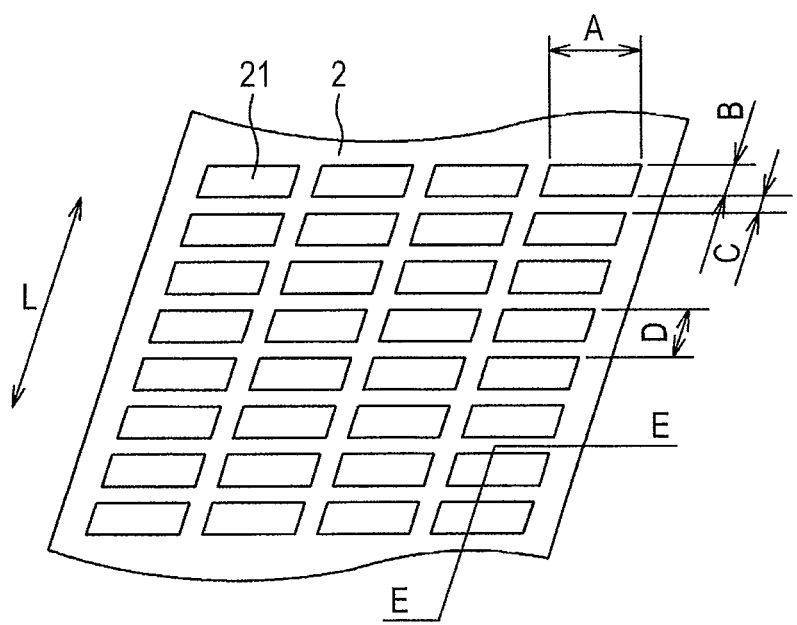
FIG. 4 is a partially enlarged view of the ultrasound transmission/reception device.

FIG. 4 is a partially enlarged view of the ultrasound transmission/reception device 2. The ultrasound transmission/reception device 2 is composed of a plurality of cells 21 arranged in highly concentrated fashion. FIG. 4 indicates a long side direction A and a short side direction B of each cell 21, a cell spacing C, and a cell pitch D. The long axis direction L shown in FIG. 3 is also indicated. A plurality of cells 21 are arranged into a channel, and the wiring 92 is connected to each of the channels for control over the transmission and reception of ultrasonic waves.

Figure 5:
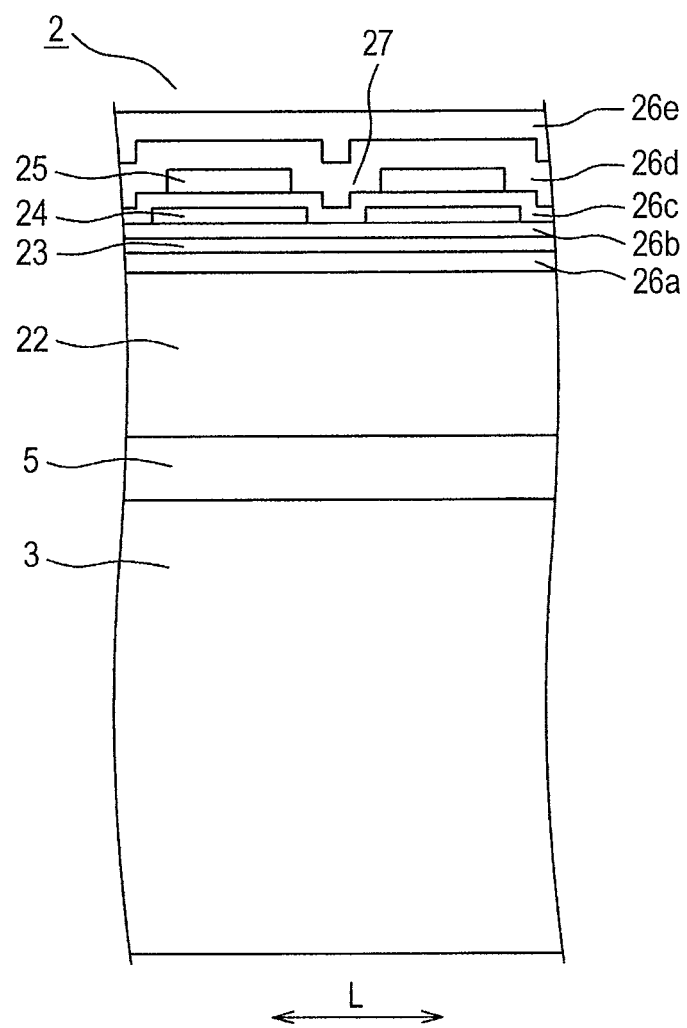
FIG. 5 is a partial cross-sectional view of a cell of the ultrasound transmission/reception device.

FIG. 5 is a cross-sectional view taken on line E-E in FIG. 4 covering two cells 21 of the ultrasound transmission/reception device 2, the view indicating the backing 3 as well. The cell 21 is made up of a substrate 22 serving as a base substrate, insulation films 26a through 26e; a lower layer electrode 23 and an upper layer electrode 25 constituting parallel plate electrodes, and a cavity 24 between the electrodes. The wall between the cells forms a rim 27. A low-modulus member 5 is interposed between each cell 2 and the backing 3. The low-modulus member 5 is a resin that bonds the cells 2 to the backing 3. That is, disposed on the substrate 22 are the cavity 24, insulation layers 26b and 26c sandwiching the cavity 24, and upper layer electrode 25 and lower layer electrode 23 sandwiching the cavity and insulation layers making up an ultrasound vibration element, with the substrate 22 supported by the backing 3 with the low-modulus member 5 interposed therebetween. FIG. 5 also shows the long axis direction L indicated in FIGS. 3 and 4. Although the material of the substrate 22 should preferably be silicon, a low thermal expansion material such as glass or ceramic may also be used instead. As the low-modulus member 5, a material such as epoxy or rubber is preferred.

When a DC voltage is applied between the lower layer electrode 23 and upper layer electrode 25 and supplemented with a pulse voltage (AC voltage), Coulomb's force causes a membrane composed of the insulation layers 26c, 26d, 26e and the upper layer electrode 25 to vibrate and emit ultrasonic waves. When reflected waves from the test object 95 enter the cell, the membrane vibrates, changing the distance between the lower layer electrode 23 and the upper layer electrode 25. This generates a displacement current that is converted to a received electrical signal. When a force is applied to the membrane during such transmission and reception, the rim 27 supporting the membrane is subjected to the force whereby ultrasonic waves are propagated to the substrate 22.

Figure 6:
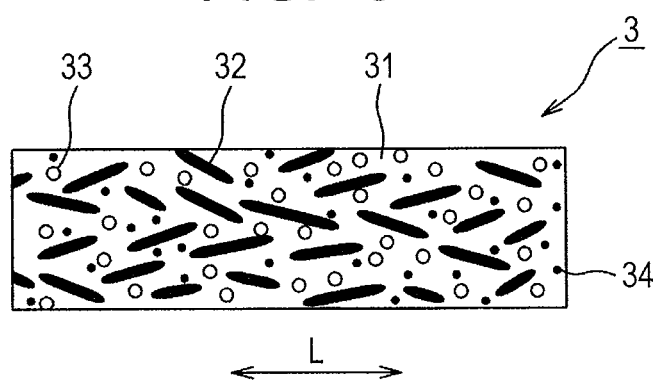
FIG. 6 is a cross-sectional view of the backing in the long axis direction thereof.

FIG. 6 is a cross-sectional view taken on line F-F in FIG. 3 of the backing 3. Carbon fiber 32 is mixed into the resin material. Preferably, the mixed carbon fiber 32 should be oriented in the long axis direction L of the backing 31, at 30 degrees or less relative to the long axis direction L. The mixed carbon fiber 32 may also be in parallel with the long axis direction L. In the latter case, the carbon fiber 32 is approximately perpendicular to the minor axis direction M. The array direction of the carbon fiber 32 follows the short side direction B of the cell 2. When the carbon fiber 32 of a low thermal expansion coefficient is mixed into the backing in the direction shown in FIG. 6, it is possible significantly to reduce the thermal expansion coefficient of the backing 3 in the long axis direction L thereof compared with the thermal expansion coefficient in the minor axis direction M. For example, the thermal expansion coefficient of about 100 ppm of a resin may be reduced to 1 to 20 ppm by suitably setting the blending ratio. Preferably, the blending ratio of the carbon fiber 32 should be 20 to 50 percent by volume. The carbon fiber 32 should preferably be 10 μm to 10 mm in length. The diameter of the carbon fiber should preferably be 2 to 100 μm. Thus when the thermal expansion coefficient of the backing in the long axis direction L thereof in the short side direction B of the cell 2 is made close to the thermal expansion coefficient of the substrate 22, it is possible to alleviate thermal stress stemming from the bonding of the ultrasound transmission/reception device 2 and backing 3 or from the process of fabrication. Distortion in the short side direction B of the cell 2 can significantly affect the performance of ultrasound transmission and reception, i.e., variance of the channels arrayed in the long axis direction L. For that reason, the distortion due to thermal stress should preferably be as small as possible. Thus the structure of this invention lowers the thermal expansion coefficient of the backing 3 by arraying the carbon fiber 32 of the backing 3 in the short side direction B of the cell 2. Furthermore, it is preferred to add particles of silica 33, tungsten 34 or the like of low thermal expansion varying in density in order to adjust thermal expansion coefficient and acoustic impedance. Where particles of low thermal expansion are added, the thermal expansion coefficient in the minor axis direction M can also be reduced, which contributes to alleviating thermal stress.

Explained next is the reflection of ultrasonic waves on the back side of the cell 21. The ultrasonic waves emitted from the cell 21 shown in FIG. 5 are released also in the back side direction of the cell 21, i.e., opposite to the direction of the test object 95 (in the frontal direction) through the rim 27. When the ultrasonic waves propagated in the back side direction are reflected and returned in the frontal direction, pulse decay time is prolonged and the waveform in effect is worsened. Also, when the ultrasonic waves are reflected from, say, the subcutaneous fat of the test object 95, returned to the cell 21, and then reflected by the back side thereof before being released in the frontal direction, the cell 21 may detect not only the ultrasonic wave echo originally reflected from the test object organism but also the ultrasonic waves reflected from the back side as mentioned above. This can cause virtual images such as ghosts to appear in the diagnostic image or can reduce the resolution of the latter image. It is thus necessary to minimize the reflection from the back side. Empirically, the reflection factor of the reflection from the back side needs to be −10 dB (31%) or less in order to prevent deterioration of the diagnostic image caused by the back side reflection.

Figure 7:
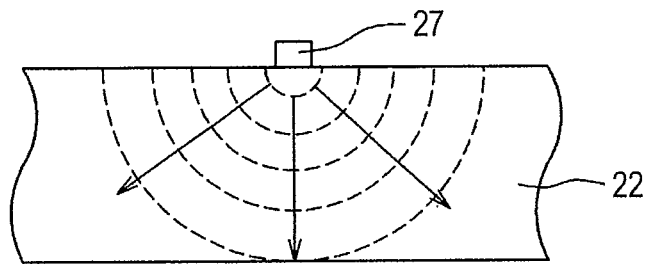
FIG. 7 is an explanatory view explaining the model of ultrasonic wave reflection.
Figure 8:
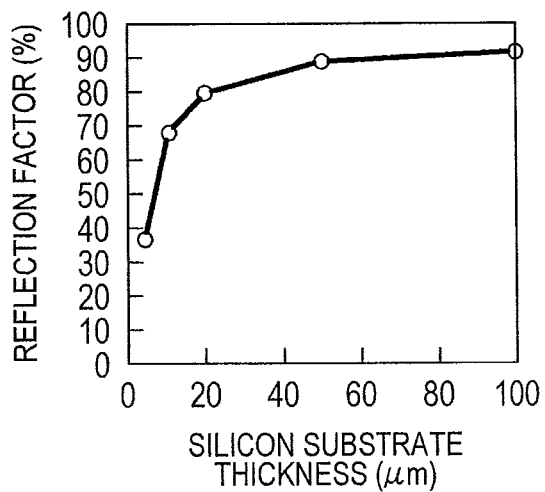
FIG. 8 is a graphic representation showing the relationship between the thickness of the ultrasound transmission/reception device substrate and reflection factors.

In order to examine the cause of the reflection from the back side of the cell 21, the inventors analyzed by the finite element method the reflection of ultrasonic waves entered at 10 MHz from a narrow rim 27 shown in FIG. 7 into the substrate 22 made of silicon. In this case, the bottom side of the substrate 22 was regarded as an acoustic absorption boundary. FIG. 8 shows the relationship between the thickness of the substrate 22 and reflection factors. Despite the absence of a reflective interface, the reflection was found to be abruptly more pronounced the thicker the substrate 22. In connection with audio equipment such as speakers, a phenomenon is known in which, if vibrating parts are small compared with the wavelength involved, sounds fail to propagate when sound pressure and volume velocity become out of phase due to the spherical propagation of the waves. Because the wavelength of the substrate 22 made of silicon was as large as approximately 8,500 μm at 10 MHz compared with the size of the rim 27 being several μm, the ultrasonic waves were found to be reflected as they spread cylindrically (indicated by broken lines) in the arrowed directions within the substrate 22 shown in FIG. 7. It was found that the conventional method of getting the acoustic impedance of the substrate to coincide with that of the backing is not effective for the CMUT that necessitates using the rim 27. The thickness of the silicon substrate should preferably be 50 μm or less.

Studies were conducted to reduce the reflection from the back side of the cell 21. The affectors involved were the thickness, Young's modulus, and density of silicon as the substrate; Young's modulus and density of the backing, width B of the cell 21, width C of the rim 27 interposed between the cells, and thickness of the low-modulus member 5. The preferred ranges of these affectors were calculated through analysis by the finite element method.

Figure 9:
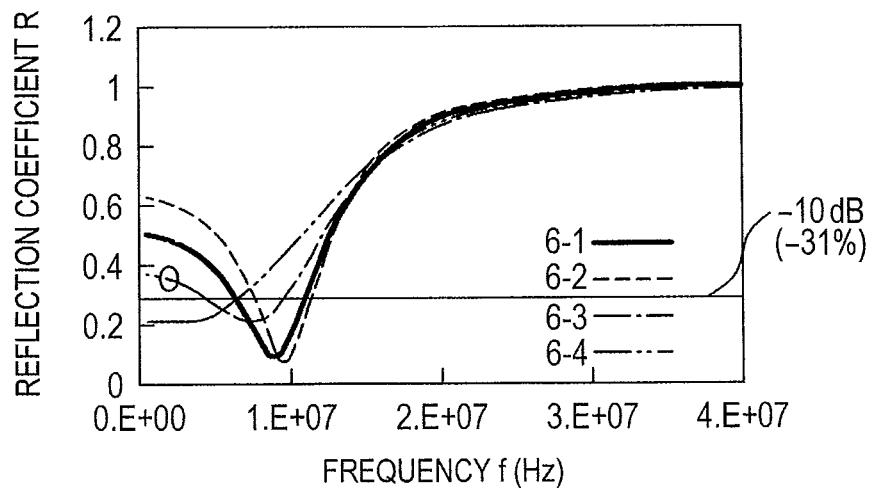
FIG. 9 is a graphic representation showing the relationship between frequencies and reflection factors from analysis of the reflection on the back side of the ultrasound transmission/reception device.

FIG. 9 shows an example of the results of the analysis, plotting the relationship between reception frequency f and the reflection coefficient R of the back side. The cell width B was set to be 25 μm, and the thickness of the substrate 22 made of silicon and that of the low-modulus member 5 were set to be 50 μm and 10 μm respectively, with the elastic modulus of the backing 3 varied. In FIG. 9, a line 6-1 stands for a reference elastic modulus of the backing 3, a line 6-2 for twice the reference elastic modulus, a line 6-3 for 0.5 times the reference elastic modulus, and a line 6-4 for 0.25 times the reference elastic modulus. Varying Young's modulus of the backing corresponds to multiplying the acoustic impedance of the backing by square roots as stated below. Since the loss caused by reflection should fall within −10 dB, i.e., within 31%, plotting a line of −10 dB in FIG. 9 reveals that the case of the line 6-3 (indicated by a hollow circle ○) provides the widest range of frequencies and should be preferred under these conditions.

Figure 10:
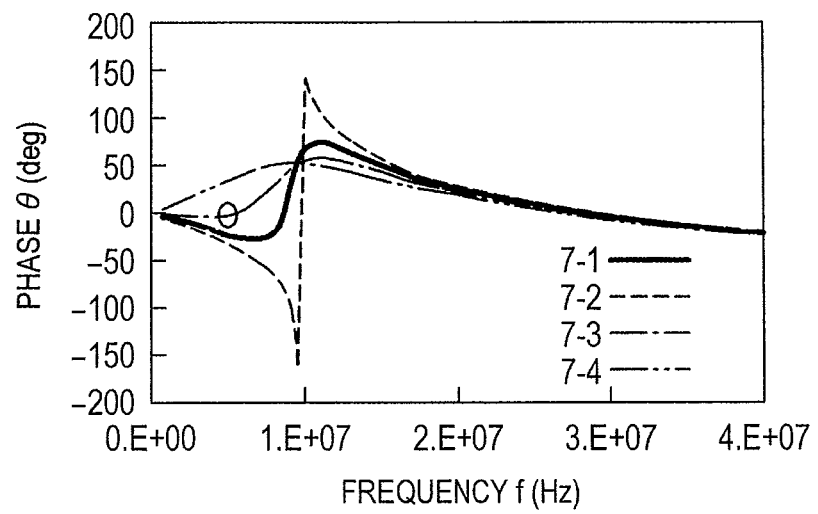
FIG. 10 is a graphic representation showing the relationship between frequencies and phases from analysis of the reflection on the back side of the ultrasound transmission/reception device.

FIG. 10 shows the relationship between the frequency f and phase θ in the results indicated in FIG. 9. A line 7-1 in FIG. 10 corresponds to the line 6-1 in FIG. 9, a line 7-2 to the line 6-2, a line 7-3 to the line 6-3, and a line 7-4 to the line 6-4. Whereas the line 7-3 indicates the result under the condition represented by the line 6-3, there are many ranges where the phase is zero, which signifies a gentle change (indicated by a hollow circle ○). This is probably attributable to the out-of-phase state being alleviated thanks to the cylindrical wave diffusion from the rim caused by mechanical vibrations of the silicon substrate 22 and the low-modulus member 5, whereby sounds toward the back side may effectively be propagated to the backing. At this point, the resonance frequency of mechanical vibrations between the silicon substrate 22 and the low-modulus member 5 is approximately 10 MHz. The reflection can then be lowered over a wideband centering on about half that resonance frequency. That is, a frequency approximately half the resonance frequency of mechanical vibrations between the substrate and the low-modulus member need only be set as the center frequency for ultrasonic drive. The short pulses over a wideband, characteristic of the CMUT, are distorted in waveform and deteriorate when the reflection is reduced over a narrowband. It was thus found that the reflection can be lowered without deterioration of short pulses when the reflection over the wideband is reduced by suitably setting the mechanical vibrations of the substrate 22 and the low-modulus member 5 and the acoustic characteristics of the backing 3.

The vibrations of the substrate 22 and the low-modulus member 5 are characterized by mechanical impedance Zm of one-degree-of-freedom vibrations. The mechanical impedance is defined by the mathematical expression 1 shown below in which M denotes the mass per unit area of the substrate 22 and k stands for the spring constant per unit area of the low-modulus member 5. In this case, the mass M per unit area is obtained from M=tρ where t stands for the thickness and ρ stands for the density of the substrate 22. The spring constant k is obtained using the mathematical expression 2 below in which E denotes Young's modulus, ν represents Poisson's ratio, and d stands for the thickness of the low-modulus member 5.

$$Zm = \sqrt{Mk} \qquad \text{[Math. 1]}$$

$$k = \frac{1-v}{(1+v)(1-2v)} \frac{E}{d} \qquad \text{[Math. 2]}$$

The following mathematical expression 3 gives the resonance frequency $f_0$ in effect when the substrate 22 is regarded as the mass M and the low-modulus member 5 as the spring constant k:

$$f_0 = \frac{1}{2\pi} \sqrt{\frac{k}{M}} \qquad \text{[Math. 3]}$$

The following mathematical expression 4 gives the acoustic impedance Z of the backing 3 in effect when Eb stands for Young's modulus, $\rho_b$ for the density, and $v_b$ for Poisson's rate of the backing:

$$Z = \sqrt{E_b \rho_b \frac{1-v_b}{(1+v_b)(1-2v_b)}} \qquad \text{[Math. 4]}$$

Under the conditions of FIGS. 9 and 10, the resonance frequency $f_0$ of one-degree-of-freedom vibrations is approximately 10 MHz. Above the resonance frequency, the reflection increases abruptly; at low frequencies, low reflection is available over a flat wideband. For this reason, half the one-degree-of-freedom resonance frequency $f_0$ may be set as the center frequency, so that low reflection may be made available within the range of ¼ to ¾ times the frequency $f_0$ constituting a frequency band of 100%.

FIGS. 11 through 14 are contour drawings of reflection factors obtained through analyses performed in like manner by the finite element method, the reflection factors plotting the acoustic impedance Z of the backing versus the mechanical impedance Zm where the substrate 22 is regarded as the mass and the low-modulus member as the spring constant. In these drawings, dashed lies denote the condition under which the mechanical impedance is equal to the acoustic impedance.

Figure 11:
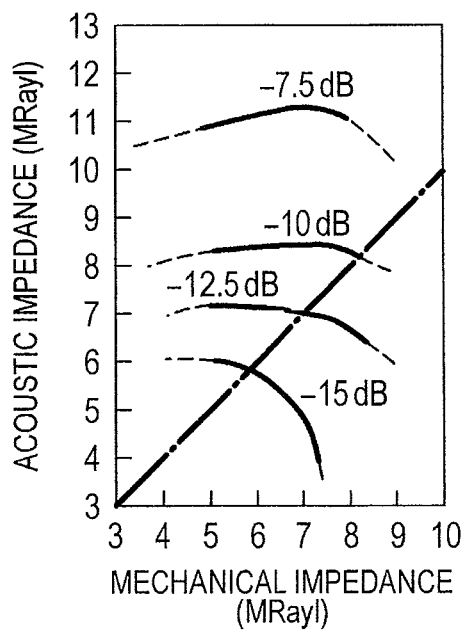
FIG. 11 is a contour drawing of reflection factors at ¼ of the resonance frequency $f_0$ between the backing and the low-modulus member as a result of analysis by the finite element method.

FIG. 11 shows contours of the reflection factors resulting from analysis by the finite element method at a frequency ¼ times the resonance frequency $f_0$ of the backing 3 and the low-modulus member 5.

Figure 12:
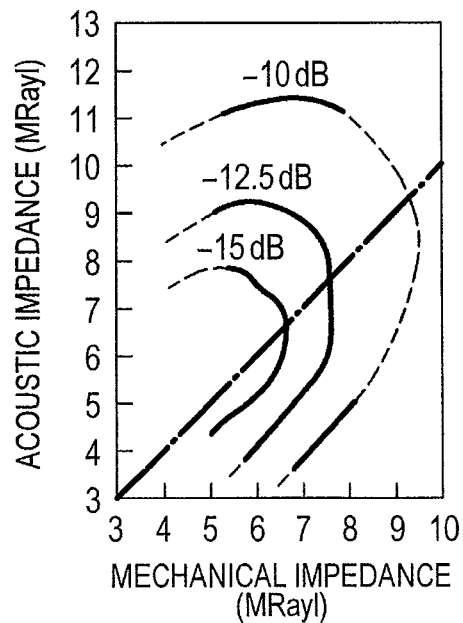
FIG. 12 is a contour drawing of reflection factors at ½ of the resonance frequency $f_0$ between the backing and the low-modulus member as a result of analysis by the finite element method.

FIG. 12 shows contours of the reflection factors resulting likewise from analysis by the finite element method at a frequency half the resonance frequency $f_0$ of the backing 3 and the low-modulus member 5.

Figure 13:
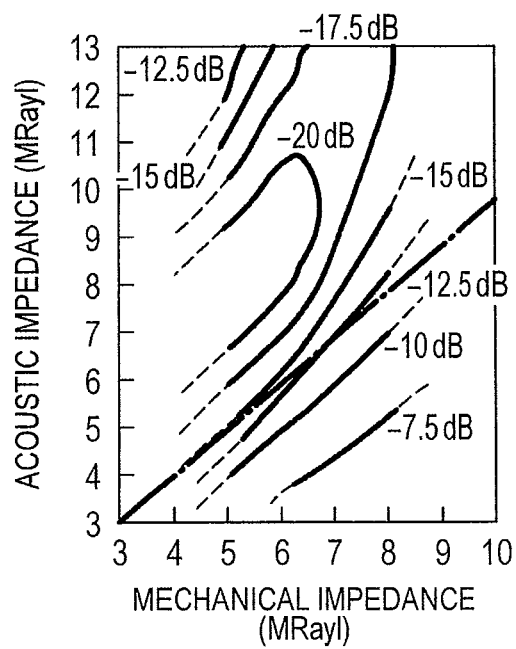
FIG. 13 is a contour drawing of reflection factors at ¾ of the resonance frequency $f_0$ between the backing and the low-modulus member as a result of analysis by the finite element method.

FIG. 13 shows contours of the reflection factors resulting likewise from analysis by the finite element method at a frequency ¾ times the resonance frequency $f_0$ of the backing 3 and the low-modulus member 5.

Figure 14:
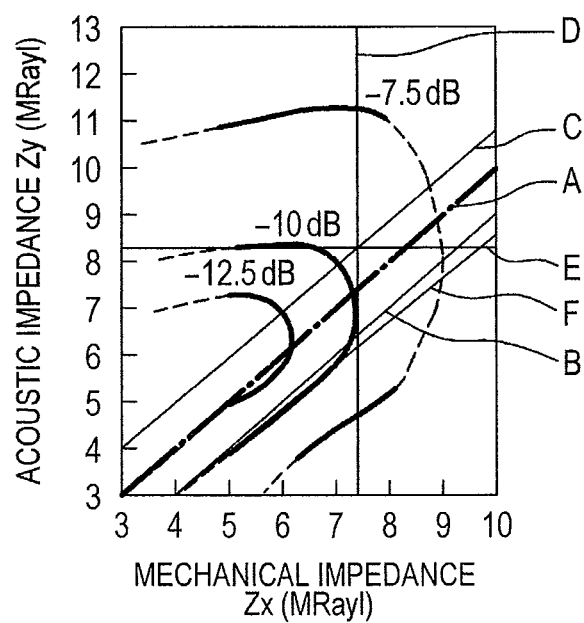
FIG. 14 is a contour drawing summarizing the maximum reflection factors shown in FIGS. 11, 12 and 13 as a result of analysis by the finite element method.

FIG. 14 is a contour drawing summarizing the maximum reflection factors shown in FIGS. 11, 12 and 13, the contours showing regions where the reflection factors are small over a wideband, the regions being preferred for reducing the back side reflection.

A straight line A in FIG. 14 denotes a line along which the mechanical impedance is equal to the acoustic impedance of the backing. The most preferred range is included over this line. And straight lines B and C with the straight line A disposed therebetween indicate the range where the acoustic impedance reads ±1 MRayls. This range flanked by the straight lines may be stipulated as a range in which the mechanical impedance is substantially equal to the acoustic impedance of the backing, whereby the back side reflection can be reduced. That is, the acoustic impedance of the backing may be set to be within ±1 MRayls ($10^6$ kg/m² s) of the mechanical impedance formed by the substrate and the low-modulus member. Also, the mechanical impedance formed by the substrate and the low-modulus member may be set to be approximately equal in value to the acoustic impedance of the backing.

Also in FIG. 14, the ranges where the reflection factors of −10 dB or less are available occur where the mechanical impedance formed by the low-modulus member 5 and substrate 22 is 7.4 MRayls or less and where the acoustic impedance of the backing 3 is 8.3 MRayls or less. The region where the reflection factors are −10 dB or less is stipulated as the region enclosed by straight lines D, E and F. If Zx denotes the value of the mechanical impedance formed by the mass of the substrate and the spring constant of the low-modulus member and Zy represents the value of the acoustic impedance of the backing, the region in question is defined as one that satisfies the mathematical expressions 5, 6 and 7 below at the same time, i.e., the range in which the back side reflection may be reduced.

$$Zx \leq 7.4 \text{ MRayls } (10^6 \text{ kg/m}^2 \text{ s}) \qquad \text{[Math. 5]}$$

$$Zy \leq 8.3 \text{ MRayls } (10^6 \text{ kg/m}^2 \text{ s}) \qquad \text{[Math. 6]}$$

$$Zy \geq 0.883 Zx - 0.532 \text{ MRayls } (10^6 \text{ kg/m}^2 \text{ s}) \qquad \text{[Math. 7]}$$

According to the above-described embodiment, for the CMUT-equipped ultrasound probe, the range of values of the mechanical impedance formed by the mass of the substrate and the spring constant of the low-modulus member and the range of values of the acoustic impedance of the backing are stipulated in such a manner as to lower the reflection of ultrasonic waves released toward the back side, whereby high-quality diagnostic images are acquired.

REFERENCE SIGNS LIST

1 Ultrasound probe
2 Ultrasound transmission/reception device
3 Backing
4 Flexible substrate
5 Low-modulus member
21 Cell
22 Substrate
23 Lower layer electrode
24 Cavity
25 Upper layer electrode
26a, 26b, 26c, 26d, 26e Insulation films
27 Rim
31 Backing
32 Carbon fiber
33 Silica
34 Tungsten
41 Resin
42 Wire
43 Case
44, 45, 46 Resins
47 Sealing resin
91 Connector
92 Wiring
94 Acoustic lens
95 Test object
97 Circuit substrate
98 Connecting terminal

The invention claimed is:

1. An ultrasound probe comprising:
an ultrasound vibration element constituted on a substrate by a cavity, by insulation layers with the cavity interposed therebetween, and by an upper layer electrode and a lower layer electrode with the cavity and the insulation layers interposed therebetween, the substrate being supported by a backing with a low-modulus member interposed therebetween, the ultrasound vibration element being vibrated by application of a direct-current voltage and an alternating-current voltage between the lower layer electrode and the upper layer electrode,
wherein the backing has an acoustic impedance falling within ±1 MRayls ($10^6$ kg/m² s) of a mechanical impedance formed by the substrate and the low-modulus member,
wherein the backing includes carbon fibers integrated into a base material arranged substantially parallel to a long axis side thereof and oriented within 30 degrees or less relative to the long axis side, and
wherein the backing on the long axis side thereof has a smaller thermal expansion coefficient than on a minor axis side thereof.

2. The ultrasound probe according to claim 1, wherein the mechanical impedance is formed by the mass of the substrate and by a spring constant of the low-modulus member.

3. The ultrasound probe according to claim 1, wherein the mechanical impedance formed by the substrate and the low-modulus member is made to have substantially the same value as the acoustic impedance of the backing.

4. The ultrasound probe according to claim 1, wherein, if Zx denotes the mechanical impedance formed by the mass of the substrate and by the spring constant of the low-modulus member and Zy represents the value of the acoustic impedance of the backing, then the values Zx and Zy are made to fall within ranges meeting the following three expressions:

$$Zx \leq 7.4 \text{ MRayls}(10^6 \text{ kg/m}^2 \text{ s}),$$

$$Zy \leq 8.3 \text{ MRayls}(10^6 \text{ kg/m}^2 \text{ s}), \text{ and}$$

$$Zy \geq 0.883 Zx - 0.532 \text{ MRayls}(10^6 \text{ kg/m}^2 \text{ s}).$$

5. The ultrasound probe according to claim 1, wherein the substrate is a silicon substrate.

6. The ultrasound probe according to claim 5, wherein the silicon substrate has a thickness of 50 μm or less.

7. The ultrasound probe according to claim 1, wherein the backing is a resin containing carbon fiber.

8. The ultrasound probe according to claim 7, wherein the resin is added with particles of silica, tungsten or a substance of low thermal expansion varying in density.

9. The ultrasound probe according to claim 1, wherein approximately half the resonance frequency of mechanical vibrations of the substrate and the low-modulus member is set as the center frequency of ultrasonic drive.

10. The ultrasound probe according to claim 1,
wherein the backing is a resin including carbon fiber, and
wherein a direction having a smaller thermal expansion coefficient, where the carbon fiber is disposed substantially in parallel, coincides with a direction of a short side of an ultrasound probe cell.

11. An ultrasound diagnostic device for obtaining an ultrasound diagnostic image of a test object, the ultrasound diagnostic device comprising the ultrasound probe according to claim 1.

* * * * *